US006694799B2

(12) United States Patent
 Small

(10) Patent No.: US 6,694,799 B2
(45) Date of Patent: Feb. 24, 2004

(54) METHOD AND APPARATUS FOR DETECTION OF PARTICLES

(75) Inventor: Jeanne Rudzki Small, Spokane, WA (US)

(73) Assignee: Eastern Washington University, Cheney, WA (US)

( * ) Notice: Subject to any disclaimer, the term of this patent is extended or adjusted under 35 U.S.C. 154(b) by 0 days.

(21) Appl. No.: 10/082,528

(22) Filed: Feb. 22, 2002

(65) Prior Publication Data

US 2003/0159498 A1 Aug. 28, 2003

(51) Int. Cl.[7] ................. G01H 17/00; G01N 21/00; G01N 21/27
(52) U.S. Cl. ............... 73/24.02; 73/24.03; 73/24.06; 73/590; 73/643; 250/339.06; 250/340; 250/339.13
(58) Field of Search ............. 73/24.01, 24.02, 73/24.03, 24.06, 643, 590; 250/339.06, 339.12, 339.13, 340

(56) References Cited

U.S. PATENT DOCUMENTS

| | | | |
|---|---|---|---|
| 4,255,971 A | 3/1981 | Rosencwaig | |
| 4,808,828 A | 2/1989 | Kitamori et al. | 250/458.1 |
| 5,444,541 A | 8/1995 | Small et al. | |
| 5,596,146 A | 1/1997 | Waller et al. | 73/590 |
| 5,701,012 A | 12/1997 | Ho | 250/461.2 |
| 5,866,430 A | 2/1999 | Grow | |
| 5,895,922 A | 4/1999 | Ho | 250/492.1 |
| 5,938,617 A | 8/1999 | Vo-Dinh | |
| 5,999,250 A | 12/1999 | Hairston et al. | 356/73 |
| 6,070,093 A | 5/2000 | Oosta et al. | |
| 6,236,455 B1 | 5/2001 | Autrey et al. | |

OTHER PUBLICATIONS

Johnson, R., "Postal Service Mulls Bioparticle Detector for Anthrax Fight", Nov. 5, 2001, pp. 1–3, URL: http://www.eetimes.com/story/OEG20011105S0051.
Eversole et al., "Continuous, Rapid Biological Aerosol Detection with the Use of UV Fluorescence: Outdoor Test Results", Field Analytical Chemistry and Technology, 3(4–5):249–259, 1999.
Hill et al., "Real–Time Measurement of Fluorescence Spectra from Single Airborne Biological Particles", Field Analytical Chemistry and Technology, 3(4–5):221–239, 1999.
Egerev et al., "Laser–Induced Cavitation: Statistics, Monte Carlo Modeling and Experiment", Proc. SPIE vol. 3916, pp. 210–217, Biomedical Optoacoustics, 2000.
McCracken et al., "UV–Visible Spectroscopy of Bacteria and Environmental Particles", Biophysical Journal, vol. 82, No. 1, Part 2 of 2, Jan. 2002, abstract 210–Pos., p. 43a.

(List continued on next page.)

Primary Examiner—Daniel S. Larkin
(74) Attorney, Agent, or Firm—Wells St. John P.S.

(57) ABSTRACT

The invention includes a particle detection system that detects bioparticles in a sample utilizing a sensor device that receives photoacoustic signals from a sample. The invention includes a system for distinguishing biologically active particles from non-biologically active particles in a sample utilizing a transducer to receive a laser induced photoacoustic signal from the sample and a fluorescence detector to receive laser induced fluorescence. The invention includes a method of screening a sample for the presence of one or more particle types by subjecting a sample to laser light and measuring at least one photonic response and at least one acoustic response are measured from the sample to produce a sample composite data set which is compared to a signature data set from a control sample. The invention also includes methods for detecting a change in the particle composition within a test area.

14 Claims, 2 Drawing Sheets

OTHER PUBLICATIONS

Preston et al., "Pulsed–Laser Photoacoustics Studies of Vegetative Bacteria and Bacterial Endospores", Biophysical Journal, vol. 82, No. 1, Part 2 of 2, Jan. 2002, abstract 204–Pos, p. 42a.

Libertini et al., "Toward Single–Particle Photoacoustics", biophysical Journal, vol. 82, No. 1, Part 2 of 2, Jan. 2002, abstract 205–Pos, p. 42a.

Gordon et al., "Identification of Fourier Transform Infrared Photoacoustic Spectral Features for Detection of *Aspergillus flavus* Infection in Corn", Int. J. Food Microbiol. 35:179–86(1997).

US 2001/0018848 A1, Autrey et al., "Multi–Band Transducer for Photoacoustic Detection", Pub. Date Sep. 6, 2001.

US 2001/0022657 A1, Autrey et al., "Photoacoustic Spectroscopy Apparatus and Method", Pub. Date Sep. 20, 2001.

Walt et al., "Biological Warfare Detection", Analytical Chemistry, vol. 72, No. 23, pp. 738A–746A, Dec. 2000.

Sales Brochure, Quantum Northwest, Inc., Flash 100 Cuvette Holder for Laser spectroscopy.

Sales Brochure, Quantum Northwest, Inc., QNW 3000 Complete Photoacoustic System.

METHOD AND APPARATUS FOR DETECTION OF PARTICLES

The U.S. Government has a paid-up license in this invention and the right in limited circumstances to require the patent owner to license others on reasonable terms as provided for by the terms of Contract No. N00014-99-1-1056, awarded by the Office of Naval Research.

TECHNICAL FIELD

In particular aspects, the invention pertains to a particle detection system and methods for the detection and identification of particles in a sample.

BACKGROUND OF THE INVENTION

Particle detection and monitoring can be of great importance for assessing environmental health risks. Various types of particles, including biological pathogens, other types of biological particles, allergens, and pollutants, can pose serious health and safety concerns. Many of these particle types can exist naturally in the environment, some of which become a health risk only at increased levels. Others can be artificially introduced into the environment by human activities including for example, industrial activities, biological warfare and bio-terrorism. The ability to detect and identify potentially harmful particles in an environment can be desired for timely particle containment and decontamination of an affected area.

Often it is difficult to distinguish viable bioparticles from nonviable bioparticles or inert particles. Current methods directed toward such determination are often unreliable and time consuming. Such problems may result in a potential for increased exposure. Additionally, the methods presently available can be cost-prohibitive due to such factors as the need for specialized personnel, or expensive reagents, equipment, or analysis techniques.

It would be desirable to develop methods for detecting bioparticles and methods for distinguishing bioparticles from non-bioparticles. It would also be desirable to develop methods to monitor particle levels in an environment.

SUMMARY OF THE INVENTION

In one aspect, the invention encompasses a particle detection system for detecting bioparticles in a sample. The particle detection system includes a sample collector having a sample outlet. The particle detection system also includes a sensor device which receives the sample and measures at least one type of photoacoustic signal from the sample.

In one aspect, the invention encompasses a system for distinguishing biological particles from non-biological particles in a sample. The system includes a chamber that retains the sample and a laser that directs emitted laser light through the sample. A transducer mounted proximate the chamber receives acoustic signals from the sample. A fluorescence detector mounted proximate the sample receives light emitted by the sample. The system utilizes the information received from the sample by the fluorescence detector and by the transducer to distinguish biologically active particles from non-biologically active particles.

In one aspect, the invention encompasses a method of screening a sample for the presence of one or more particle types. A sample is subjected to laser light to produce at least one photonic response and at least one acoustic response which are measured to establish a sample composite data set. The sample composite data set is compared to a signature data set which is obtained from a control sample having a known particle composition. The signature data set is a fingerprint of the known composition of the control sample. Comparison of the signature data set and the sample composite data set is indicative of a presence or absence within the sample of particles identified by the signature data set.

In one aspect, the invention encompasses a method of detecting a change in the particle composition within a test area. Particles are collected and concentrated into a volume of liquid to produce a test sample. A sample is provided into a sensor device where one or more types of photoacoustic signals are induced from the test sample. A photoacoustic measurement is obtained and compared to reference data which is generated from one or more reference samples that have been obtained and processed identically to the test sample.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

The invention can encompass methods which can be utilized for generating information about particles contained in various samples. In particular aspects, the invention encompasses methods for generating information about biological particles (bioparticles) present in a sample. For purposes of the present description, the term "bioparticle" can refer to any form of microorganism including both viable and nonviable microorganisms, and any fragment and any subcomponent of such microorganisms, including nucleic acids and proteins.

A process encompassed by one aspect of the present invention and which can be utilized for generating information about particle composition of samples, is described with reference to a flowchart in FIG. 1. At initial step 10, a sample is collected for analysis. The sample can comprise particles, and can be collected, for example, from the air, from a surface, or from a liquid. Particle size for collection step 10 is not limited to a specific size and can be, for example less than or equal to about fifty microns.

Sample collection step 10 can include forming a liquid sample. A liquid sample can be formed by adding a liquid to suspend particles obtained from a non-liquid, such as particles collected from air or from a surface. An appropriate liquid for purposes of particle suspension can comprise, for example water. It is to be understood that, in certain embodiments, the liquid utilized for suspension purposes can comprise additional reagents such as, for example, an agent, such as a detergent or surfactant, to assist in particle suspension. Alternatively, methods of the present invention can utilize a sample collected from the air without an addition of any liquid.

In addition to the features described above, sample collection step 10 can include concentration of particles within a fluid. The fluid can comprise, for example, air or a liquid. The sample concentration can include concentration of the particles within the sample until a desired light absorbance or extinction is achieved. For purposes of the present invention, a sample can be concentrated to a predetermined absorbance measurement which can be from about 0.001 to about 0.5 absorbance units (AU), preferably between about 0.001 and about 0.005 AU. The energy of light for absorbance or extinction determination during sample collection step 10 is not limited to any specific wavelength. Preferably, the wavelength of light used for absorbance or extinction measurements during sample collection will be a wavelength of light that can be utilized in analysis of the collected sample (see below).

Figure 2:
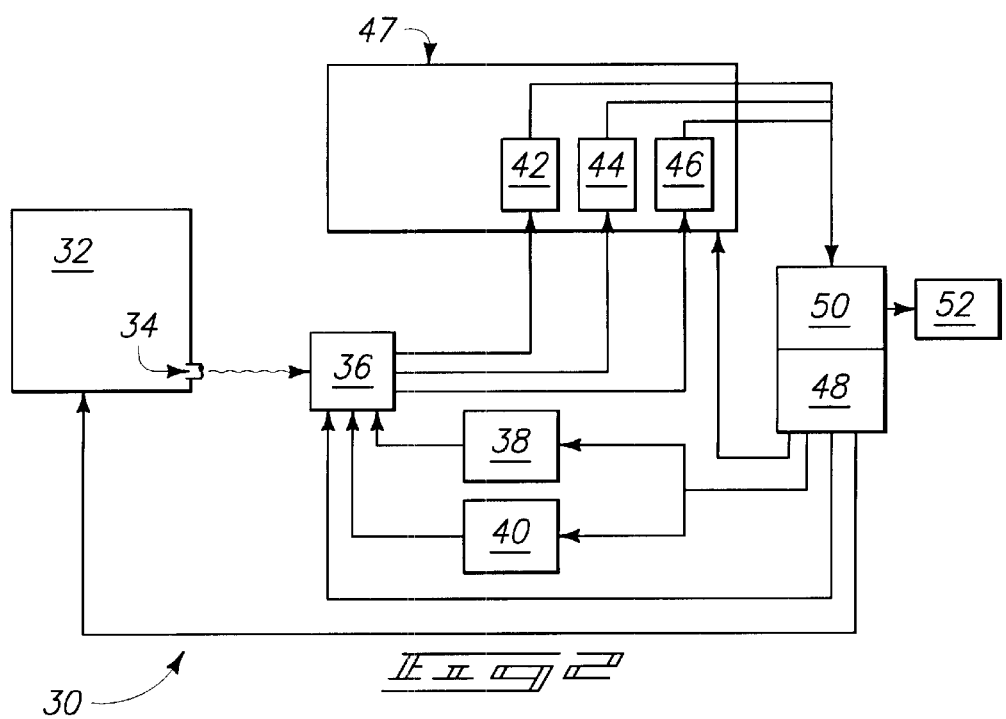
FIG. 2 is a schematic view showing a sample collection and analysis system used in performing particular aspects of the present invention.

A particle detection system 30 comprising an exemplary sample collector 32 is shown in FIG. 2. Sample collector 32 can be configured for one or more of collection of particles, suspension of particles in a fluid, and concentration of particles. Sample collector 32 can comprise an outlet 34 configured to provide the collected sample to a sample chamber 36 for sample analysis. Sample collector 32 can be further configured to selectively collect particles within a specific size range such as, for example particles between from about one micron to about ten microns.

Sample collector 32 is not limited to a specific type of sample collector. One commercially available bio-aerosol sample collector that can be utilized for purposes of the present invention is a Bioguardian™ produced by InnovaTek, Inc.

Referring again to FIG. 1, a sample collected by step 10 can be provided to a sample chamber in step 12. As shown in FIG. 2, particle detection system 30 can comprise a sample chamber which can be in receiving relation relative to sample outlet 34. The providing step is not limited to any specific method and can comprise, for example, providing sample aliquots to the sample chamber or providing a continuous flow between the collector and the sample chamber. Providing sample to the sample chamber can utilize any of numerous available transfer devices such as, for example, mechanical delivery, manual delivery, or fluidics transfer devices, such as a flow cell.

Figure 1:
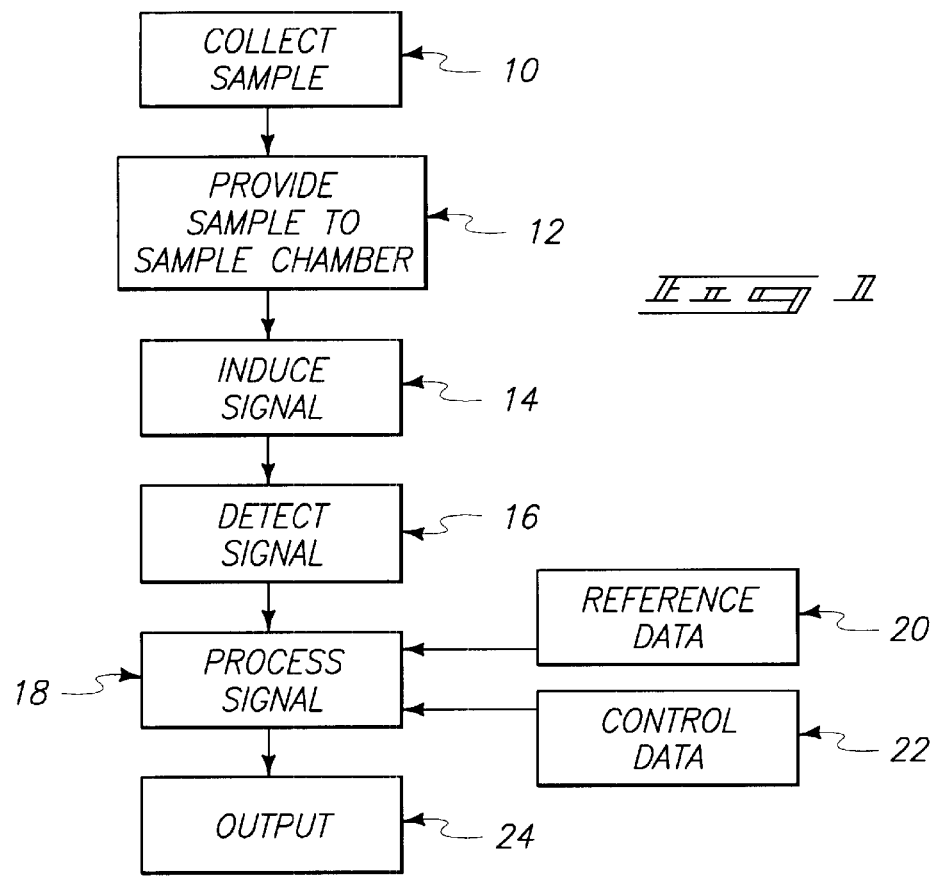
FIG. 1 is a flow chart diagram illustrating a particular aspect of the present invention.

Referring to step 14 of FIG. 1, a collected sample can be induced to produce a signal. Signal induction step 14 can comprise subjecting the sample to an energy source which can comprise one or more wavelengths between about 250 nm and about 700 nm. Induction step 14 can comprise subjecting a sample to one or more incident light beams which can comprise, but are not limited to laser light. In embodiments utilizing a light source or a laser light source, a wavelength can be, for example, from greater than about 250 nm to less than about 600 nm. In particular embodiments, one or more inducing light sources can emit light comprising at least one of 266 nm, 337 nm, 355 nm, 420 nm, 470 nm, 520 nm, and 570 nm wavelengths.

Referring to FIG. 2, sample chamber 36 can be positioned proximate one or more inducers 38, 40 configured to induce one or more signals from a sample. Numerous energy sources are available for use as inducers for purposes of the present invention and can comprise, for example, a laser (including but not limited to a light laser), and a non-laser light source. For purposes of the present description, when an inducer 38, 40 comprises a photonic emitter, the inducer can be referred to as a photo-inducer. Likewise, induction by a photo-inducer can be referred to as photo-induction. For purposes of the present invention, photo-induction can comprise induction with a continuous light beam or with a pulsed light beam. In particular embodiments of the present invention utilizing pulsed laser induction, photo-induction can comprise low energy photo-induction comprising less than or equal to about 80 $\mu J$ of energy per laser pulse. Alternatively, pulsed laser photo-induction can comprise high energy photo-induction, high energy photo-induction comprising from greater than about 80 $\mu J$ to less than or equal to about 900 $\mu J$ of energy per laser pulse.

As shown in FIG. 2, particle detection system 30 can comprise two inducers 38 and 40. Inducers 38 and 40 can be identical or can be different. Inducers 38 and 40 can comprise, for example, two photon sources, such as two lasers. For instance, inducer 38 can comprise a first laser that emits a first wavelength laser beam and inducer 40 can comprise a second laser that emits a second wavelength laser beam.

Alternatively, detection system 30 can comprise a single inducer which can be configured to emit single wavelength energy or can comprise a single inducer configured to emit one or more of a multiple wavelength beam or a plurality of beams having different wavelengths. It is to be understood that the invention also contemplates embodiments comprising greater than two inducers. If a sample is induced at multiple wavelengths it can be possible to increase the information obtained by signal detection. It can be advantageous to utilize a plurality of wavelengths for induction to increase a likelihood of obtaining a set of signals capable of classification of a particle type, or, in some instances even identification of a specific particle type (discussed below).

Signals that can be induced by the induction methods utilized in the present invention include, but are not limited to, acoustic signals and photonic signals. Photonic signals can include light absorbance, light scatter, light transmittance, and fluorescence. Acoustic signals can comprise sonic waves including ultrasonic waves. For purposes of the present description, when induction comprises photonic induction, an acoustic signal generated in the sample can be referred to as a photoacoustic signal.

In addition to the features described above, sample chamber 36 can be configured to stir the sample during the inducing step. It can be advantageous to stir the sample while inducing to maintain the particles in suspension. Sample chamber 36 can be configured to control the temperature of a sample. The temperature of a sample can be maintained from about 4° C. to about 95° C., preferably from about 30° C. to about 80° C., and more preferably at about 37° C.

Referring again to FIG. 1, once a signal has been induced signal detection step 16 can be performed. The detection system 30 depicted in FIG. 2 can be configured for detection of one or more of a variety of signals. A plurality of signal detectors 42, 44 and 46 can be comprised by the detection system and can be configured for signal detection according to methods of the present invention. As shown in FIG. 2, detector system 30 can comprise three detectors 42, 44 and 46. It is to be understood that the invention contemplates embodiments wherein detector system 30 comprises one, two or greater than three detectors. Preferably, detector system 30 comprises three or more detectors. As shown in FIG. 2, a plurality of detectors 42, 44, 46 can be comprised by a single sensor device 47.

A variety of detectors are available for use for purposes of the present invention. Such detectors can include, but are not limited to, various forms of transducers, energy meters, photo multiplier tubes, photodiodes, and charge coupled device detectors. It is to be understood that the present invention encompasses numerous combinations of detector devices. Selection of the number and combination of detector devices for any specific embodiment of the present invention can be determined by the specific application for which it will be utilized. For instance, sensor device 47 of FIG. 2 can comprise, one or more energy meters, a photomultiplier tube, and a transducer.

As shown in FIG. 2, a sensor device 47 can be positioned proximate sample chamber 36 and independently of inducers 38 and 40. Alternatively, inducers 38 and 40 can be comprised by a common integrated sensor unit (not shown) containing one or more detectors 42, 44, 46. Additionally, sample chamber 36 can be comprised by the integrated sensor unit (not shown). An exemplary commercially available integrated sensor device which can be utilized for purposes of the present invention is Quantum Northwest's multi-sensor, Model No. QNW3010.

For purposes of the present description, photoacoustic signals induced utilizing the methods of the present invention can be classified into two types. A first type of photoacoustic signal can comprise, for example, signals that result from a low energy induction (discussed above). For example, the first type of photoacoustic signal can result from subjecting a sample to a laser pulse comprising energy of less than or equal to about 80 $\mu J$. Measurement of one or more first type of photoacoustic signals can be used, for example, to determine an amount of an incident laser pulse absorbed by the sample. It can be advantageous to measure an absorbance of the sample using photoacoustic methods to obtain an accurate absorbance measurement without light scatter effects.

A second type of photoacoustic measurement that can be obtained utilizing the methods of the present invention is measurements of photoacoustic signals that result from subjecting a sample to high energy induction (discussed above). This second type of photoacoustic signal can be generated by, for example, subjecting a sample to a pulse of laser light comprising energy from greater than about 80 $\mu J$ to less than or equal to about 900 $\mu J$. Measurement of the second type of photoacoustic signal can be used to detect certain particle-solvent effects induced within the sample. Solvent-particle effects can be specific to a particle type. Accordingly, measurement of photoacoustic signals generated from solvent-particle effects can be useful for particle detection and particle identification purposes.

One solvent-particle effect that can be detected utilizing the methods of the present invention is cavitation. For at least some particle types, cavitation can involve bubble formation which is induced by, for example, high laser pulse energies. The acoustic signals generated by cavitation can be due to one or more of bubble formation, bubble oscillation, and bubble collapse. Such cavitation events can utilize different induction energy for different types of particles. Accordingly, photoacoustic signals can be measured after induction by, for example, high energy laser pulses, and can be useful for detection of particle types in a sample, for classification of particle types in a sample and, in particular embodiments, identification of specific particles in a sample.

The photoacoustic signals induced during induction step 14 (FIG. 1) can be detected in detection step 16 utilizing one or more transducers configured for detection of sonic waves. Accordingly, the sensor device shown in FIG. 2 can comprise at least one transducer.

Photonic signals generated by induction step 14 of FIG. 1 can be detected in step 16 by providing one or more of an energy meter, a photomultiplier tube, and a charged coupled device (CCD) detector. For instance, the detector system 30 shown in FIG. 2 can comprise sensor device 47 configured to detect a fluorescence signal utilizing at least one of a photomultiplier tube and a CCD detector. In embodiments that utilize a photomultiplier tube, the photomultiplier tube can be used in conjunction with one or more of a monochromater and an optical filter.

The induction and generation of a fluorescence signal can be particle specific. Accordingly, fluorescence measurements obtained utilizing methods of the present invention can be useful for detection and identification of specific particle types within a sample. Specific energy wavelengths for induction and fluorescence detection can be chosen based upon the types of particles to be monitored, detected or identified by the particular embodiment of the present invention. Fluorescence measurements obtained by methods of the present invention can comprise measurements obtained at a single wavelength or can comprise measurements obtained over a range of wavelengths. Detection of fluorescence can be performed, for instance, at one or more wavelengths from between about 300 nm and 700 nm.

Referring again to FIG. 1, when an energy beam induces a sample in step 14, the amount of an energy beam that is transmitted through a sample or that is scattered from a sample can depend upon the particle composition of the sample. Accordingly, measurements of transmittance and scattering and determination of absorbance can be useful for monitoring, detecting, or identifying particles in a sample. Signal detection step 16 can therefore include measurement of one or both of transmittance and scattering of the incident beam. Accordingly, sensor device 47, as comprised by the exemplary particle detector system 30 in FIG. 2, can be configured for measuring one or both of transmittance and scattering. For instance, sensor device 47 can comprise one or more energy meters configured to receive one or both of scattered and transmitted energy from an induced sample.

The present invention encompasses embodiments that determine one or more of energy transmittance, absorbance, and scattering by a sample at a single time point. The invention also encompasses embodiments that monitor one or more of energy transmittance, absorbance, and scattering by an induced sample at a number of time points.

It can be advantageous to measure one or more photonic energy signals over a period of time to monitor or detect changes in the sample during the time period. Photonic signal measurements obtained over a period of time can be useful for detecting or monitoring effects, such as particle breakdown or denaturation events. For instance, DNA has a characteristic change in light absorbance at or near wavelength 260 nm that occurs due to denaturation (melting) of the DNA as the sample is heated. Utilizing methods of the present invention, it can be possible to detect and distinguish DNA in a sample comprising a plurality of particle types by heating the sample over a period of time and obtaining a plurality of photonic signal measurements over the time period. Accordingly, sample chamber 36 of FIG. 2 can be configured to heat the sample over a period of time during which photonic signals are induced and detected.

Referring to signal processing step 18 of FIG. 1, data obtained from the detected signal 16 can be processed and an output 24 can be generated. Processing step 18 can include generating information about at least one of the presence (or absence) of one or more particle types, the concentration of one or more particle types, and the identification of one or more particle types. As shown in FIG. 1, processing step 18 can comprise comparison of signal measurements obtained from a sample to one or both of reference data 20 and control data 22 (discussed below). For purposes of the present description, the term 'control data' refers to data obtained from one or more samples having a known composition, and the term 'reference data' refers to data which has been collected from one or more reference samples. Preferably, each reference sample used for the collection of reference data has been collected and processed by methods identical to the collecting and processing of a test sample to be compared. In addition, reference data 20 can comprise data from reference samples that have been collected from the same area or location to be tested by the test sample.

A comparison between signal data obtained from a test sample and reference data can comprise one or more of comparing fluorescence data obtained from a test sample with fluorescence reference data, comparing energy absorbance data obtained from a test sample to reference absorbance data, comparing energy transmittance data obtained from a test sample with transmittance reference data, comparing low energy induction photoacoustic data obtained from a test sample with low energy induction photoacoustic reference data, and comparing high energy induction photoacoustic data obtained from a test sample with high energy induction photoacoustic reference data. In addition, signal processing step 18 can comprise creating a composite data set for a test sample. A composite data set can comprise, for example, at least two, and preferably three or more, of fluorescence data, energy absorbance data, energy transmittance data, low energy induction photoacoustic data, and high energy induction photoacoustic data. The composite data set obtained from a test sample, can be compared to composite data sets obtained from one or more reference samples.

When signal processing step 18 comprises a comparison between data collected from a test sample and reference data, the comparison can be utilized, for example, for one or both of detecting a particular particle type in an area from which the sample was collected and detecting a change in particle composition within a collection area. A change in particle composition can include a change in concentration of one or more particle types within an area or a change in the type of particle present in an area. Accordingly, a background particle composition can be determined for an area by collecting and processing samples from a test area over a period of time using the methods of the present invention. The collection of reference samples over a period of time can comprise obtaining individual reference samples at specified intervals within the time period. Alternatively, reference samples can be obtained from an area continuously over a time period by for example providing a continuous flow of fluid to be tested and obtaining data from the continuous flow of test fluid. For example, referring to the particle detection system depicted in FIG. 2, collector device 32 can be configured to continuously collect, concentrate, and provide sample fluid to sample chamber 36. Particle detection system 30 can be configured to induce and detect signals from the continuous flow at specified time points. Once test data has been obtained and processed for a given time point, the data can be combined with data from previous time points which can collectively be used as a background reference for future test data.

In embodiments of the present invention that utilize control data 22 for comparison during test sample signal processing step 18, the control data can comprise data collected from individual control samples, with each control sample having a known particle composition. Comparison between data obtained from test samples and control data can comprise comparison between a test sample composite data set (discussed above) and composite data sets comprising control data, each composite data set being obtained from a known composition. Individual control composition data sets can be created utilizing the sample data collection techniques of the present invention. A control composite data set that comprises composite data from measurements obtained from a control sample having a known particle composition can be a fingerprint of the known composition. Accordingly, the fingerprint can be used as a unique identifier of the known composition. Comparison between a composite data set obtained from a test sample and a signature data set that is a fingerprint of a known composition can determine the presence or absence within the test sample of particles comprised by the known composition. Accordingly, comparison between a sample composite data set that is a fingerprint of a known particle composition can be used to identify specific particles contained in the test sample.

The methods of the present invention also include creation of a library of signature data sets, with the library including a collection of individual signature data sets which have each been collected from a known composition. A plurality of signature data sets comprised by a library can be individually compared to a composite data set obtained from a test sample to identify at least some of the particles present in the test sample.

Although comparison between a test sample and control samples has been described in terms of comparison between test composite data sets and control composite data sets, it is to be understood that the present invention encompasses individual comparison of one or more of a fluorescence measurement, an absorbance measurement, a transmittance measurement, a low-energy induction photoacoustic measurement, and a high-energy induction photoacoustic measurement obtained from a test sample with data obtained from one or more control samples.

An exemplary embodiment of signal processing according to the present invention is described with reference to FIG. 2. As shown, particle detection system 30 can comprise a signal processor 50. Detection system 30 can be configured to generate output information from signals received by detectors 42, 44, and 46. Signal processor 50 can be configured to receive the output information generated by the sensor device and can be configured to analyze the information by performing a comparison to one or both of reference data and control data as described above. Processor 50 can additionally be configured to recognize one or both of the presence of a specified particle type or an increase in the concentration of a specified particle type in a test sample relative to a reference. Further, processor 50 can be configured such that recognition of one or more of the presence or an increase in concentration of a specified particle type can trigger the processor to generate an alarm 52. Alarm 52 can comprise, for example, a visual signal or an audible signal.

Particle detection system 30 can also comprise a controller 48. Controller 48 can be configured to control operation of one or more of sample chamber 36, sensor device 47, inducers 38, 40 and collector 32. Controller 48 can also be in electrical communication with processor 50 and, in particular applications, both processor 50 and controller 48 can be comprised by a single computer.

In a particular embodiment of the present invention, particle detection system 30 can be configured for detection of a specific type of bioparticle within a test sample. The specified type of bioparticle can comprise, for example, a bioparticle selected from the group consisting of yeast, live bacteria, dead bacteria, bacterial endospores, fungal spores, viruses, mycoplasmas, molds, allergens, nucleic acids, and proteins. Bioparticle detection can involve collection of a sample comprising, for instance, air, within collector 32. Particles in the collected air can be concentrated and can be suspended in a volume of liquid, for instance water, to create the test sample for analysis. The test sample can be provided from collector outlet 34 to sample chamber 36. The sample can be induced by, for example, pulsed laser beams emitted from one or more lasers 38 and 40.

As discussed above, a plurality of detectors 42, 44, and 46 can be utilized to obtain measurements of various signals induced in the sample. Sensor device 47 can relay the measurement data to processor 50 which can compare a composite data set generated from the test sample to a composite data set obtained from a control sample comprising the specified type of bioparticle being detected in the test sample. Upon recognition of the specified type of bioparticle in the sample, processor 50 can generate an alarm 52.

A specified type of bioparticle can have a fingerprint composite data set, as discussed above with respect to fingerprints of particle types in general. A bioparticle fingerprint can be used as a unique identifier to specifically identify the bioparticle. For example, bacteria such as *Pseudomonas aeruginosa* and *Serratia marcescens* have fingerprint composite data sets that can be produced by methods of the present invention. A comparison between the fingerprint composite data set of a specific type of bacteria and a composite data set obtained from a test sample can identify a probable presence or absence of the specific bacteria within the test sample.

Figure 3:
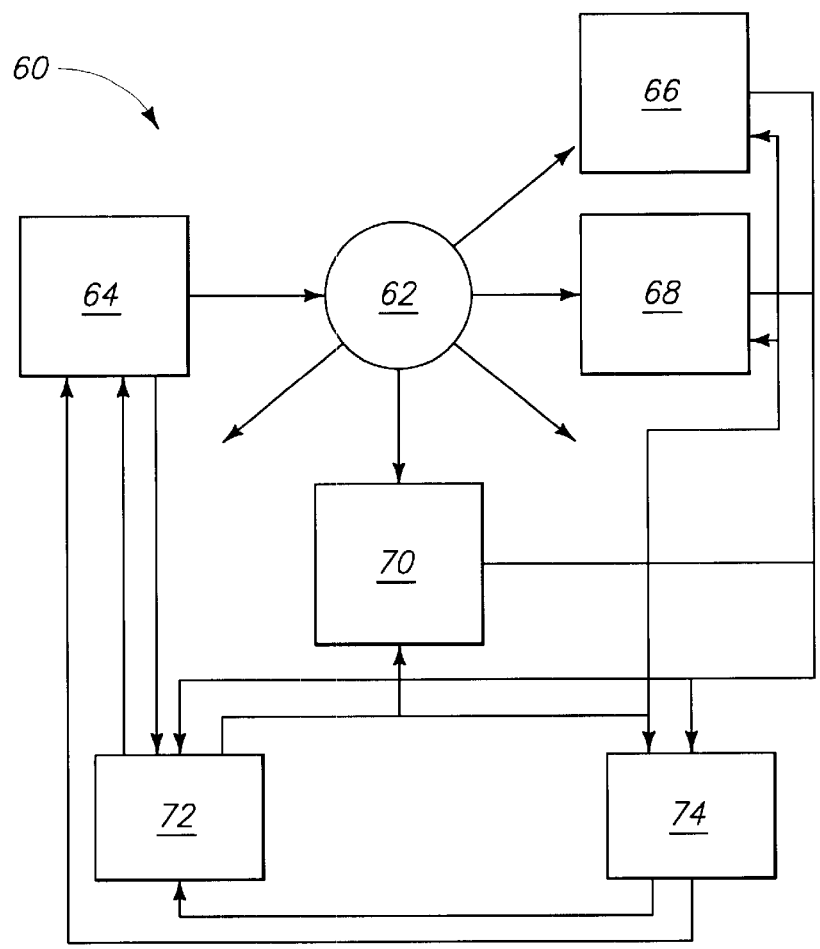
FIG. 3 is a schematic view showing an analytical system used in performing various methods of the present invention.

FIG. 3 is a diagrammatic view of a system 60 encompassed by particular aspects of the present invention which can be used for distinguishing biological particles from non-biological particles in a sample or, in particular embodiments, can be used for distinguishing biologically viable particles from non-viable particles or inert particles in a sample. Particle distinguishing system 60 shown in FIG. 3 can comprise a chamber 62 configured to retain a sample. Sample chamber 62 can comprise, for example, a cuvette or a flow cell. A laser 64 can be configured to direct emitted laser light through the sample. A transducer 66 can be mounted proximate chamber 62 and can be configured to receive one or more acoustic signals from the sample. In addition, a fluorescence detector 70 can be mounted proximate the sample and can be configured to receive light emitted by the sample. Laser light emitted from laser 64 can extend across a first axis relative to the sample. Fluorescence detector 70 can be oriented along a second axis relative to the sample wherein the second axis is substantially perpendicular to the first axis.

Particle distinguishing system 60 can be configured to use information received from the sample by fluorescence detector 70 and transducer 66 to distinguish biological particles from non-biological particles, or to distinguish biologically viable particles from non-viable or inert particles. Particle distinguishing system 60 can further comprise an absorbance detection system 68 which can be configured to determine an amount of laser light absorbed or scattered by the sample.

In addition to the features described above, particle distinguishing system 60 can comprise a controller 72 configured to control operation of absorbance detection system 68, laser 64, transducer 66, and fluorescence detector 70. In addition, particle distinguishing system 60 can comprise a signal processor 74 in data communication with absorbance detection system 68, laser 64, transducer 66, and fluorescence detector 70.

Figure 4:
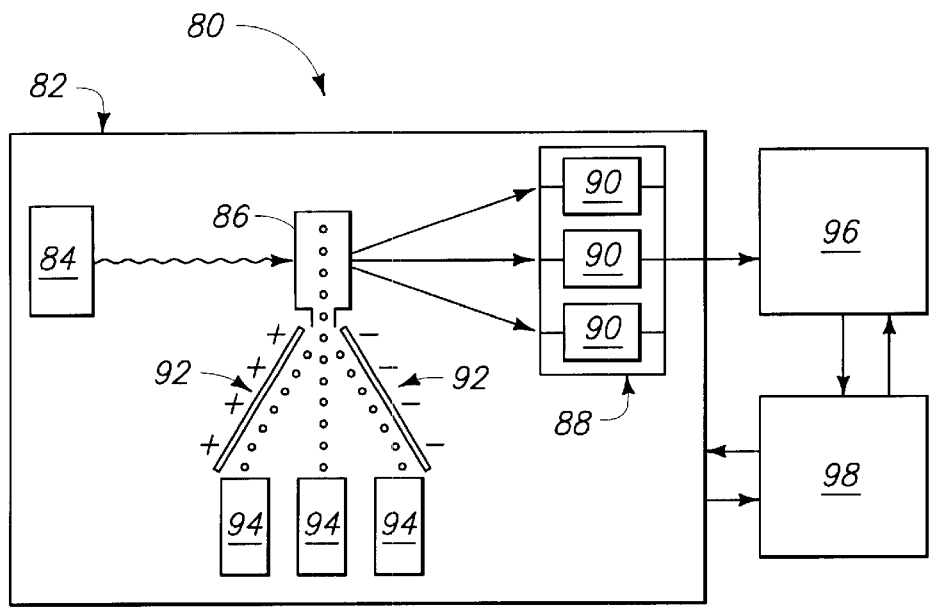
FIG. 4 is a schematic view showing incorporation of a sorting apparatus into a system of the present invention.

FIG. 4 shows a particle sorting system 80 encompassed by particular aspects of the present invention. Particle sorting system 80 can comprise a sorting module 82 such as, for instance, a flow cytometer. Sorting module 82 can comprise a sample chamber 86 configured to retain a sample comprising one or more particle types. A sensor device 88 can comprise a plurality of detectors 90 configured to detect a plurality of signals comprising one or more of a first acoustic signal, a second acoustic signal, a fluorescence emission, and a light absorbance or transmittance. Particle sorting system 80 can further comprise a laser 84 configured to direct a beam of laser light through sample reservoir 86. A signal processor 96 can be provided in data communication with the sorting module 82 of particle sorting system 80. Additionally, a controller 98 can be provided in electrical communication with the sensor and can be configured to control operation of the sorting module. Particle sorting system 80 can further comprise a component (not shown) configured to impart a charge to particles in a particle stream, and charge plates 92 positioned to deflect and thereby sort the charged particles into receptacles 94 configured for receipt of sorted particles. Alternatively, sorting system 80 can utilize a valve system (not shown) for directing the particle stream to the appropriate receptacle 94.

Particle sorting system 80 can be used, for example, to separate bioparticles from non-bioparticles or to sort potentially harmful bioparticles from benign and inert particles. Sorted samples collected in receptacles 94 can be further tested by various available chemical methods to verify the presence or absence of specific particles in each sorted sample.

In addition to the features described above, the invention can encompass embodiments configured to sterilize a test sample. For instance, the particle detection system 30 of FIG. 2 can comprise a sterilization system (not shown) which can be integrated into the sensor or into the particle collector, or which can be a separate module. Sterilization of a sample can utilize one or more of UV light irradiation, application of a disinfectant, and ozone gas treatment.

Although the invention has been described primarily with respect to bioparticle detection, it is to be understood that the methods and systems described can be adapted for detection and monitoring of non-biological particles. Such adaptations can be appropriate, for example, for monitoring emissions or detection of various particle pollutants. For instance, the above described methods can be utilized to monitor carbon emissions due to unique cavitation events that generate carbon specific photoacoustic signals.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An apparatus for inspecting particles in a sample, comprising:

a particle collector configured to collect and concentrate particles to form a sample having a pre-determined energy absorbance at a specified wavelength;

a response inducer in sample receiving relation relative to the collector and configured to induce a response from particles in the sample, the response comprising a plurality of detectable signals;

a response detector comprising a plurality of signal receivers configured to receive at least two of the plurality of detectable signals and generate output information from the received signals; and an information processor configured to receive the output information and analyze the information by comparing the information to reference data, the reference data comprising data obtained from one or both of control samples and background sample.

2. The apparatus of claim 1 wherein the plurality of signal receivers comprise one or more of a transducer, a photomultiplier tube, a photodiode, a charge coupled device detector, and an energy meter.

3. The apparatus of claim 1 wherein the particle collector is further configured to separate particles based on size and to collect particles within a size range to form the sample.

4. The apparatus of claim 3 wherein the size range is less than about fifty microns.

5. The apparatus of claim 3 wherein the size range is from about one micron to about microns.

6. The apparatus of claim 1 wherein the particle collector is configured to collect particles from air.

7. The apparatus of claim 1 wherein the particle collector is configured to suspend collected particles in liquid.

8. A method of analyzing particle content of a sample, comprising:

collecting an air sample comprising particles;

adding a liquid to the sample;

concentrating the particles in the liquid;

subjecting the sample to an incident light beam; and monitoring a photoacoustic response from the sample.

9. The method of claim 8 wherein the light beam comprises a laser beam.

10. The method of claim 9 wherein the laser beam is pulsed.

11. The method of claim 8 wherein the monitoring comprises collecting data from the photoacoustic response, and further comprising:

comparing the data to control data, the control data comprising data generated from samples having a known particle composition utilizing methods identical to the methods utilized on the sample.

12. The method of claim 8 wherein the photoacoustic response is a first photoacoustic response and further comprising monitoring at least one additional emission comprising one or more of a second acoustic response and a fluorescence emission.

13. The method of claim 8 wherein the concentrating comprises concentrating the particles until a predetermined level of light absorbance is reached.

14. The method of claim 8 further comprising measuring one or more of absorbance of the incident light beam and scattering of the incident light beam.

* * * * *

UNITED STATES PATENT AND TRADEMARK OFFICE
CERTIFICATE OF CORRECTION

PATENT NO. : 6,694,799 B2
DATED : February 24, 2004
INVENTOR(S) : Small

Page 1 of 1

It is certified that error appears in the above-identified patent and that said Letters Patent is hereby corrected as shown below:

Column 11,
Line 27, replace "about microns" with -- about ten microns --.

Signed and Sealed this

Thirteenth Day of July, 2004

JON W. DUDAS
*Acting Director of the United States Patent and Trademark Office*